United States Patent
Fischell et al.

(10) Patent No.: US 8,157,856 B2
(45) Date of Patent: Apr. 17, 2012

(54) STENT HAVING A MULTIPLICITY OF UNDULATING LONGITUDINALS

(76) Inventors: Robert E. Fischell, Dayton, MD (US);
David R. Fischell, Fair Haven, NJ (US);
Tim A. Fischell, Nashville, TN (US)

( * ) Notice: Subject to any disclaimer, the term of this patent is extended or adjusted under 35 U.S.C. 154(b) by 507 days.

(21) Appl. No.: 11/804,710

(22) Filed: May 18, 2007

(65) Prior Publication Data
US 2007/0255384 A1   Nov. 1, 2007

Related U.S. Application Data

(63) Continuation of application No. 11/179,424, filed on Jul. 12, 2005, which is a continuation of application No. 10/662,792, filed on Sep. 15, 2003, now abandoned, which is a continuation of application No. 10/345,531, filed on Jan. 16, 2003, now Pat. No. 6,716,240, which is a continuation of application No. 09/596,074, filed on Jun. 16, 2000, now Pat. No. 6,547,817, which is a continuation of application No. 09/263,518, filed on Mar. 5, 1999, now Pat. No. 6,086,604, which is a continuation of application No. 08/864,221, filed on May 28, 1997, now Pat. No. 5,879,370, which is a continuation of application No. 08/202,128, filed on Feb. 25, 1994, now Pat. No. 5,643,312.

(51) Int. Cl.
*A61F 2/82* (2006.01)
(52) U.S. Cl. ..................... 623/1.15; 623/1.13
(58) Field of Classification Search ............... 623/1.15, 623/1.13
See application file for complete search history.

(56) References Cited

U.S. PATENT DOCUMENTS

| | | | |
|---|---|---|---|
| 3,657,744 A * | 4/1972 | Ersek | 128/898 |
| 4,503,469 A | 3/1985 | Dotter | |
| 4,553,545 A | 11/1985 | Maass et al. | |
| 4,580,568 A | 4/1986 | Gianturco | |

(Continued)

FOREIGN PATENT DOCUMENTS
EP    593 136    12/1984
(Continued)

OTHER PUBLICATIONS

Lawrence et al., *Percutaneous Endovascular Graft: Experimental Evaluation*, 1986 RSNA Annual Meeting, *Radiology*, vol. 163, pp. 357-60 (May 1987).

(Continued)

*Primary Examiner* — Thomas J Sweet
*Assistant Examiner* — Rebecca Straszheim
(74) *Attorney, Agent, or Firm* — Wood, Phillips, Katz, Clark & Mortimer

(57) ABSTRACT

A method for implanting a balloon expandable stent at a site within a passageway of a curved coronary article. The stent includes at least two longitudinally spaced apart circumferential rings. At least one longitudinally extending connector extends between adjacent rings. The connector has at least one turn back portion that can expand or contract in length while being passed through a curved passageway. The stent is disposed on a stent delivery catheter having an inflatable balloon. The stent delivery catheter and the stent is delivered through the passageway to the site of implementation with the connector member expanding or contracting in length to facilitate delivery and placement of the stent. The stent is expanded at the site of implantation by inflating the balloon to force the stent radially outward against the wall of the coronary artery.

9 Claims, 4 Drawing Sheets

U.S. PATENT DOCUMENTS

| | | | |
|---|---|---|---|
| 4,655,771 A | 4/1987 | Wallsten | |
| 4,681,110 A | 7/1987 | Wiktor | |
| 4,733,665 A | 3/1988 | Palmaz | |
| 4,739,762 A | 4/1988 | Palmaz | |
| 4,768,507 A | 9/1988 | Fischell | |
| 4,795,458 A | 1/1989 | Regan | |
| 4,800,882 A | 1/1989 | Gianturco | |
| 4,830,003 A | 5/1989 | Wolff | |
| 4,856,516 A * | 8/1989 | Hillstead | 606/194 |
| 4,878,906 A | 11/1989 | Lindemann et al. | |
| 4,886,062 A | 12/1989 | Wiktor | |
| 4,907,336 A | 3/1990 | Gianturco | |
| 4,954,126 A | 9/1990 | Wallsten | |
| 4,969,458 A | 11/1990 | Wiktor | |
| 4,994,071 A * | 2/1991 | MacGregor | 606/194 |
| 5,019,085 A | 5/1991 | Hillstead | |
| 5,061,275 A | 10/1991 | Wallsten | |
| 5,102,417 A * | 4/1992 | Palmaz | 606/195 |
| 5,104,404 A * | 4/1992 | Wolff | 623/1.16 |
| 5,109,090 A | 4/1992 | Mongoin et al. | |
| 5,116,365 A | 5/1992 | Hillstead | |
| 5,133,732 A | 7/1992 | Wiktor | |
| 5,135,536 A | 8/1992 | Hillstead | |
| 5,192,307 A | 3/1993 | Wall | |
| 5,195,984 A | 3/1993 | Schatz | |
| 5,201,901 A | 4/1993 | Harada | |
| 5,266,073 A | 11/1993 | Wall | |
| 5,269,802 A | 12/1993 | Garber | |
| 5,282,824 A | 2/1994 | Gianturco | |
| 5,290,305 A | 3/1994 | Inoue | |
| 5,292,331 A | 3/1994 | Boneau | |
| 5,314,472 A | 5/1994 | Fontaine | |
| 5,405,377 A | 4/1995 | Cragg | |
| 5,421,955 A * | 6/1995 | Lau et al. | 216/48 |
| 5,443,498 A * | 8/1995 | Fontaine | 623/1.17 |
| 5,443,500 A | 8/1995 | Sigwart | |
| 5,449,373 A * | 9/1995 | Pinchasik et al. | 606/198 |
| 5,496,365 A | 3/1996 | Sgro | |
| 5,507,767 A | 4/1996 | Maeda et al. | |
| 5,507,771 A | 4/1996 | Gianturco | |
| 5,514,154 A * | 5/1996 | Lau et al. | 623/1.15 |
| 5,527,354 A | 6/1996 | Fontaine et al. | |
| 5,569,295 A * | 10/1996 | Lam | 606/198 |
| 5,591,197 A | 1/1997 | Orth et al. | |
| 5,603,721 A * | 2/1997 | Lau et al. | 606/195 |
| 5,632,771 A * | 5/1997 | Boatman et al. | 623/1.15 |
| 5,643,312 A * | 7/1997 | Fischell et al. | 623/1.15 |
| 5,674,278 A | 10/1997 | Boneau | |
| 5,733,303 A * | 3/1998 | Israel et al. | 623/1.15 |
| 5,814,472 A | 9/1998 | Miki et al. | |
| 5,879,370 A * | 3/1999 | Fischell et al. | 623/1.16 |
| 6,086,604 A * | 7/2000 | Fischell et al. | 606/198 |
| 6,258,116 B1 * | 7/2001 | Hojeibane | 623/1.16 |
| 6,375,660 B1 | 4/2002 | Fischell et al. | |
| 6,547,817 B1 * | 4/2003 | Fischell et al. | 623/1.16 |
| 6,716,240 B2 * | 4/2004 | Fischell et al. | 623/1.16 |

FOREIGN PATENT DOCUMENTS

| | | |
|---|---|---|
| EP | 433 011 | 6/1991 |
| EP | 472 731 | 3/1992 |
| EP | 540 290 | 5/1993 |
| EP | 566 807 | 10/1993 |
| EP | 579 523 | 1/1994 |
| GB | 1 205 743 | 9/1970 |
| GB | 2 189 150 | 10/1987 |
| JP | 6-41745 | 6/1994 |
| WO | WO 95/31945 | 6/1994 |

OTHER PUBLICATIONS

Mirisch et al., *Percutaneously Placed Endovascular Grafts for Aortic Aneurysms: Feasibility Study, Radiology*, vol. 170, pp. 1033-1037.

Fallone et al., *Elastic Characteristics of the Self-Expanding Metallic Stents, Investigative Radiology*, vol. 23, pp. 370-376, (May 1988).

Charnsangavej et al., *Stenosis of the Vena Cava: Preliminary Assessment of Treatment with Expandable Metallic Stents, Radiology*, 1986, 161-295-98.

Rosch et al., *Gianturco Expandable Stents in Experimental and Clinical Use*, Mar. 24, 1987.

Wallace et al., *Tracheobronchial Tree: Expandable Metallic Stents Used in Experimental and Clinical Applications Work in Progress*, Radiology, 158:309-12 (1986).

Rosch et al., *Experimental Intraheptic Partacural Anastomosis: Use of Expandable Gianturco Stents, Radiology*, 162:481-85 (1987).

Bosch et al., *Modified Gianturco Expandable Wire Stents in Experimental and Clinical Use Arm Radiol*, 31:100-03 (1988).

Charnsangavej et al., *A New Expandable Metallic Stent for Dilation of Stenotic Tubular Structures Experimental and Clinical Evaluations, Houston Medical Journal*, vol. 3, Jun. 1987.

Rosch et al., *Gianturco Expandable Wire Stents in the Treatment of Superior Vena Cava Syndrome Recurring After Maximum Tolerance Radiation, Cancer*, 60:1243-46 (1987).

Yoshioka et al., *Self-Expanding Endovascular Graft: An Experimental Study in Dogs, AJR*, 151: 673-76 (1988).

Simonds et al., *Use of Experimental Metal Stents in the Treatment of Bronchial Obstruction, Thorax*, 44:;680-81 (1989).

Duprat et al., *Flexible Balloon-Expandable Stent for Small Vessels, Radiology*, 162:276-78 (1987).

Jury Verdict (Damages) of *Cordis Corporation v. Boston Scientific Corporation and Scimed Life Systems, Inc.* et al., Civil Action No. 97-550-SLR and *Cordis Corporation v. Boston Scientific Corporation* et al., Civil Action No. 98-197 (SLR).

Jury Verdict (Liability) *Cordis Corporation v. Boston Scientific Corporation and Scimed Life Systems, Inc.* et al., Civil Action No. 97-550-SR and *Cordis Corporation v. Boston Scientific Corporation* et al., Civil Action No. 98-197 (SLR).

Nov. 20, 2000, Pretrial Hearing of *Boston Scientific Corporation* et al. v. *Cordis Corporation*, Civil Action No. 98-19 (SLR) and *Cordis Corporation v. Boston Scientific Corporation* et al., Civil Action No. 98-197 (SLR).

Nov. 21, 2000, Trial Transcript of *Cordis Corporation v. Medtronic Ave, Inc.* et al., Civil Action No. 97-550 (SLR) and *Cordis Corporation v. Boston Scientific Corporation* et al., Civil Action No. 98-197 (SLR).

Nov. 27, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Nov. 28, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Nov. 29, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Nov. 30, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Dec. 1, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Dec. 4, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Dec. 5, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Dec. 6, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Dec. 7, 2000, Trial Transcript of *Cordis Corporation v. Medtronic Ave., Inc.* et al., Civil Action No. 97-550 (SLR) and *Cordis Corporation v. Boston Scientific Corporation* et al., Civil Action No. 98-197 (SLR).

Dec. 8, 2000, Trial Transcript of *Cordis Corporation* v. *Medtronic Ave., Inc.* et al., Civil Action No. 97-550 (SLR) and *Cordis Corporation* v. *Boston Scientific Corporation* et al., Civil Action No. 98-197 (SLR).

Dec. 11, 2000, Trial Transcript of *Cordis Corporation* v. *Medtronic Ave., Inc.* et al., Civil Action No. 97-550 (SLR) and *Cordis Corporation* v. *Boston Scientific Corporation* et al., Civil Action No. 98-197 (SLR).

Dec. 12, 2000, Trial Transcript of *Cordis Corporation* v. *Medtronic Ave., Inc.* et al., Civil Action No. 97-550 (SLR) and *Cordis Corporation* v. *Boston Scientific Corporation* et al., Civil Action No. 98-197 (SLR).

Dec. 13, 2000, Trial Transcript of *Cordis Corporation* v. *Medtronic Ave., Inc.* et al., Civil Action No. 97-550 (SLR) and *Cordis Corporation* v. *Boston Scientific Corporation* et al., Civil Action No. 98-197 (SLR).

Dec. 14, 2000, Trial Transcript of *Cordis Corporation* v. *Medtronic Ave., Inc.* et al., Civil Action No. 97-550 (SLR) and *Cordis Corporation* v. *Boston Scientific Corporation* et al., Civil Action No. 98-197 (SLR).

Dec. 15, 2000, Trial Transcript of *Cordis Corporation* v. *Medtronic Ave., Inc.* et al., Civil Action No. 97-550 (SLR) and *Cordis Corporation* v. *Boston Scientific Corporation* et al., Civil Action No. 98-197 (SLR).

Feb. 9, 2001, Trial Transcript (Inequitable Conduct) of *Cordis Corporation* v. *Medtronic Ave, Inc.*, et al, Civil Action No. 97-550 and *Cordis Corporation* v. *Boston Scientific Corporation* et al., Civil Action No. 98-197 (SLR).

Feb. 12, 2001, Trial Transcript (Inequitable Conduct) of *Cordis Corporation* v. *Medtronic Ave, Inc.*, et al, Civil Action No. 97-550 and *Cordis Corporation* v. *Boston Scientific Corporation* et al., Civil Action No. 98-197 (SLR).

Mar. 28, 2002, Order re Post Trial Motions of *Cordis Corporation* v. *Medtronic Ave., Inc.*, Civil Action No. 97-550 (SLR).

Mar. 28, 2002, Opinion re Post Trial Motions of *Cordis Corporation* v. *Medtronic Ave., Inc.*, Civil Action No. 97-550 (SLR).

*Cordis Corporation* v. *Boston Scientific Corporation and Scimed Life Systems, Inc.*, Brief in Support of BSC's Motions for Judgement as a Matter of Law with Respect to U.S. Patent Nos. 5,643,312 and 5,879,370, Civil Action No. 98-197-SLR.

*Cordis Corporation* v. *Boston Scientific Corporation, and Scimed Life Systems, Inc.*, Answering Brief in Opposition to BSC's Motion for JMOL on the Fischell '312 and '370 Patents, Civil Action No. 98-197-SLR.

*Cordis Corporation* v. *Boston Scientific Corporation and Scimed Life Systems, Inc.*, BSC's Reply Brief in Support of BSC's Motions for Judgement as a Matter of Law with Respect to U.S. Patent Nos. 5,643,312 and 5,879,370, Civil Action No. 98-197-SLR.

*Cordis Corporation* v. *Boston Scientific Corporation and Scimed Life Systems, Inc.*, Opening Brief in Support of Cordis' JMOL Motion Against Boston Scientific on Claim 44 of the Palmaz '762 Patent and Claim 25 of the Fischell '370 Patent, Civil Action No. 97-550 (SLR) and Civil Action No. 98-197-SLR.

*Cordis Corporation* v. *Boston Scientific Corporation and Scimed Life Systems, Inc.*, BSC's Brief in Opposition to Cordis' JMOL Motion Regarding the Applicability of the Reverse Doctrine of Equivalents to Claim 25 of U.S. Patent No. 5,879,370, Civil Action No. 98-197-SLR.

*Cordis Corporation* v. *Boston Scientific Corporation and Scimed Life Systems, Inc.*, Reply Brief in Support of Cordis' Motion for JMOL Against BSC on Claim 44 of the Palmaz '762 Patent and Claim 25 of the Fischell '370 Patent, Civil Action No. 97-550-SLR and *Cordis Corporation* v. *Boston Scientific Corporation* et al., Civil Action No. 98-197 (SLR).

*Cordis Corporation* v. *Boston Scientific Corporation and Scimed Life Systems, Inc.*, BSC's Post-Trial Brief in Support of Finding that U.S. Patent Nos. 5,643,312 and 5,879,370 are Unenforceable due to Inequitable Conduct, Civil Action No. 98-197 (SLR).

*Cordis Corporation* v. *Boston Scientific Corporation and Scimed Life Systems, Inc.*, BSC's Post-Trial Brief in Support of Finding that U.S. Patent Nos. 5,643,312 and 5,879,370 are Unenforceable due to Inequitable Conduct, Civil Action No. 98-197 (SLR).

*Cordis Corporation* v. *Boston Scientific Corporation and Scimed Life Systems, Inc.*, Reply Brief in Support of Defendants' Motion for Summary Judgment of Unenforceability due to Inequitable Conduct, Civil Action No. 98-197-SLR.

*Cordis Corporation* v. *Boston Scientific Corporation and Scimed Life Systems, Inc.*, Defendants' Markman Memorandum on Claim Construction, Civil Action No. 98-197-SLR.

*Cordis Corporation* v. *Boston Scientific Corporation and Scimed Life Systems, Inc.*, Reply Brief in Support of Defendants' Motion for Summary Judgement of Invalidity Under 35 U.S.C. Section 112, Paragraph 2 (Claim Indefiniteness), Civil Action No. 98-197-SLR.

*Cordis Corporation* v. *Boston Scientific Corporation and Scimed Life Systems, Inc.*, Reply Brief in Support of Defendant's Motion for Summary Judgement of Noninfringement, Civil Action No., 98-197-SLR.

*Cordis Corporation* v. *Boston Scientific Corporation and Scimed Life Systems, Inc.*, Opening Export Report of David C. Cumberland, M.D., Civil Action No. 98-197 SLR.

*Cordis Corporation* v. *Boston Scientific Corporation and Scimed Life Systems, Inc.*, Rebuttal Export of David C. Cumberland, M.D., Civil Action No. 98-197-SLR.

*Cordis Corporation* v. *Boston Scientific Corporation and Scimed Life Systems, Inc.*, Supplemental Export Report of David C. Cumberland, M.D. Civil Action No. 98-197-SLR.

*Cordis Corporation* v. *Boston Scientific Corporation and Scimed Life Systems, Inc.*, Opening Expert Report of Andrew S. Douglas, Ph.D., Civil Action No. 98-197-SLR.

*Cordis Corporation* v. *Boston Scientific Corporation and Scimed Life Systems, Inc.*, Rebuttal Expert Report of Andrew S. Douglas, Ph.D., Civil Action No. 98-197-SLR.

*Cordis Corporation* v. *Boston Scientific Corporation and Scimed Life Systems, Inc.*, Supplemental Expert Report of Andrew S. Douglas, Ph.D., Civil Action No. 98-197-SLR.

*Cordis Corporation* v. *Boston Scientific Corporation and Scimed Life Systems, Inc.*, Boston Scientific Corporation and Scimed Life Systems, Inc.'s Notice Pursuant to 35 U.S.C. §282, Civil Action No. 97-550-SLR and *Cordis Corporation* v. *Boston Scientific Corporation* et al., Civil Action No. 98-197 (SLR).

*Cordis Corporation* v. *Boston Scientific Corporation and Scimed Life Systems, Inc.*, Memorandum Order dated Sep. 7, 2000, Civil Action No. 98-197-SLR.

*Cordis Corporation* v. *Boston Scientific Corporation and Scimed Life Systems, Inc.*, Order dated Nov. 1, 2000 Denying Defendant's Motion for Summary Judgment of Invalidity, Civil Action No. 98-197-SLR.

*Cordis Corporation* v. *Boston Scientific Corporation and Scimed Life Systems, Inc.*, Order dated Nov. 1, 2000 Summary Judgement of Infringement, Civil Action No. 98-197-SLR.

*Cordis Corporation* v. *Boston Scientific Corporation and Scimed Life Systems, Inc.*, Videotaped Deposition of Robert E. Fischell, Ph.D dated Nov. 16, 1999, Civil Action No. 98-197-SLR.

*Cordis Corporation* v. *Boston Scientific Corporation and Scimed Life Systems, Inc.*, Videotaped Deposition of Robert E. Fischell, Ph.D dated Jan. 4, 2000, Civil Action No. 98-197-SLR.

*Cordis Corporation* v. *Boston Scientific Corporation and Scimed Life Systems, Inc.*, Videotaped Deposition of Robert E. Fischell, Ph.D dated Jan. 5, 2000, Civil Action No. 98-197-SLR.

*Cordis Corporation* v. *Boston Scientific Corporation and Scimed Life Systems, Inc.*, Videotaped Deposition of Robert E. Fischell, Ph.D dated Jan. 6, 2000, Civil Action No. 98-197-SLR.

*Cordis Corporation* v. *Boston Scientific Corporation and Scimed Life Systems, Inc.*, Videotaped 30 (b) (6) Deposition of Robert E. Fischell, Ph.D dated Jan. 6, 2000, Civil Action No. 98-197-SLR.

*Cordis Corporation* v. *Boston Scientific Corporation and Scimed Life Systems, Inc.*, Videotaped Deposition of Robert E. Fischell, Ph.D dated Jun. 15, 2000, Civil Action No. 98-197-SLR.

*Cordis Corporation* v. *Boston Scientific Corporation and Scimed Life Systems, Inc.*, Videotaped Deposition of Morton Rosenberg, Esq. Dated Feb. 3, 2000, Civil Action No. 98-197-SLR.

*Cordis Corporation* v. *Boston Scientific Corporation and Scimed Life Systems, Inc.*, Videotaped Deposition of Morton J. Rosenberg, Esq. Dated Jun. 15, 2000, Civil Action No. 98-197-SLR.

*Cordis Corporation* v. *Boston Scientific and Scimed Life Systems, Inc.*, Corrected Brief of Plaintiff-Appellant Cordis Corporation, dated Sep. 9, 2005, Civil Action No. 05-1418,-1432.
*Cordis Corporation* v. *Boston Scientific and Scimed Life Systems, Inc.*, Brief of Defendants-Cross Appellants, dated Nov. 8, 2005, Civil Action No. 05-1418,-1432.
*Cordis Corporation* v. *Boston Scientific and Scimed Life Systems, Inc.*, Corrected Reply Brief of Plaintiff-Appellant Cordis Corporation, dated Feb. 2, 2006, Civil Action No. 05-1418,-1432.
*Cordis Corporation* v. *Boston Scientific and Scimed Life Systems, Inc.*, Reply Brief of Defendants-Cross Appellants, dated Feb. 9, 2006, Civil Action No. 05-1418,-1432.
*Cordis Corporation* v. *Boston Scientific and Scimed Life Systems, Inc.*, Reply Brief of Defendants-Cross Appellants, dated Feb. 9, 2006, Civil Action No. 05-1418,-1432.
*Cordis Corporation* v. *Boston Scientific and Scimed Life Systems, Inc.*, Decision of the Federal Circuit, dated Jun. 29, 2006, Civil Action No. 05-1418,-1432.
Trial exhibits 632-640 from the IsoStent trial.
*IsoStent LLC* v. *LPL Systems, Inc.*, Deposition of David R. Fischell, M.D., dated Jul. 9, 2003, Civil Action No. 804863.
*IsoStent LLC* v. *LPL Systems, Inc.*, Deposition of Tim Fischell, M.D., dated Jul. 8, 2003, Civil Action No. 804863.
*IsoStent LLC* v. *LPL Systems, Inc.*, Videotaped Deposition of Dr. Robert E. Fischell, M.D., dated Aug. 5, 2003, Civil Action No. 804863.
*IsoStent LLC* v. *LPL Systems, Inc.*, Deposition of Robert E. Fischell, M.D., dated Jan. 15, 2004, Civil Action No. 804863.
*IsoStent LLC* v. *LPL Systems, Inc.*, Deposition of David R. Fischell, M.D., dated Jan. 14, 2004, Civil Action No. 804863.
*IsoStent LLC* v. *LPL Systems, Inc.*, Trial Transcript from Sep. 9, 2004, Civil Action No. 1-02-cv-804863.
*IsoStent LLC* v. *LPL Systems, Inc.*, Trial Transcript from Sep. 10, 2004, Civil Action No. 1-02-cv-804863.
*IsoStent LLC* v. *LPL Systems, Inc.*, Trial Transcript from Sep. 13, 2004, Civil Action No. 1-02-cv-804863.
*IsoStent LLC* v. *LPL Systems, Inc.*, Trial Transcript from Sep. 14, 2004, Civil Action No. 1-02-cv-804863.
*IsoStent LLC* v. *LPL Systems, Inc.*, Trial Transcript from Sep. 15, 2004, Civil Action No. 1-02-cv-804863.
*IsoStent LLC* v. *LPL Systems, Inc.*, Trial Transcript from Aug. 31, 2004, Civil Action No. 1-02-cv-804863.
*IsoStent LLC* v. *LPL Systems, Inc.*, Trial Transcript from Sep. 1, 2004, Civil Action No. 1-02-cv-804863.
*IsoStent LLC* v. *LPL Systems, Inc.*, Trial Transcript from Sep. 2, 2004, Civil Action No. 1-02-cv-804863.
*IsoStent LLC* v. *LPL Systems, Inc.*, Trial Transcript from Sep. 3, 2004, Civil Action No. 1-02-cv-804863.
*IsoStent LLC* v. *LPL Systems, Inc.*, Trial Transcript from Sep. 7, 2004, Civil Action No. 1-02-cv-804863.
*IsoStent LLC* v. *LPL Systems, Inc.*, Trial Transcript from Sep. 8, 2004, Civil Action No. 1-02-cv-804863.
Request for Ex Parte Reexamination of U.S. Patent 6,547,817, dated Dec. 22, 2004.
Order Denying Request for Ex Parte Reexamination, dated Mar. 15, 2005.
Petition to the Director under 37 C.F.R. § 1.181, dated Apr. 15, 2005.
Decision on Petition, dated Jun. 30, 2005.
Expert report from Boston Scientific's expert James Moore, Dec. 16, 2011.
Cordis' opening Markman brief, Dec. 16, 2011.
Boston Scientific' opening Markman brief Dec. 16, 2011.
Deposition transcript from Boston Scientific' expert James Moore Dec. 16, 2011.
Deposition transcript from Bost Scientific' expert Alan Moak, Dec. 16, 2011.
Expert Report of Professor James E. Moore, Jr., Ph.D, Dec. 16, 2011.
United States Court of Appeals' decision dated Sep. 28, 2011 in *Cordis Corporation* v. *Boston Scientific Corporation and Boston Scientific Scimed, Inc.*, case No. 2010-1311,-1316.
Deposition of David R. Fischell dated Apr. 19, 2011; in the case of *Cordis Corporation* v. *Boston Scientific Corporation* et al., In the United States District Court for the District of Delaware, Case No. 10-39-SLR.
Deposition of Robert E. Fischell dated Apr. 22, 2011; in the case of *Cordis Corporation* v. *Boston Scientific Corporation* et al., In the United States District Court for the District of Delaware, Case No. 10-39-SLR.
Deposition of Timothy Fischell, M.D. dated May 6, 2011; in the case of *Cordis Corporation* v. *Boston Scientific Corporation* et al., In the United States District Court for the District of Delaware, Case No. 10-39-SLR.
Deposition of Robert E. Fischell dated May 11, 2011; in the case of *Cordis Corporation* v. *Boston Scientific Corporation* et al., In the United States District Court for the District of Delaware, Case No. 10-39-SLR.
BSC's Fourth Supplemental Responses to Cordis's First Set of Interrogatories [No. 2], In the United States District Court for the District of Delaware, Case No. 10-39-SLR, filed May 23, 2011.
Expert Report of Professor James E. Moore, Jr., Ph.D., Regarding invalidity of U.S. Patent Nos. 6,086,604, 6,547,817, and 6,716,204 dated Jun. 20, 2011.
BSC's Third Supplemental Responses to Plaintiffs First Set of Interrogatories [No. 2], In the United States District Court for the District of Delaware, Case No. 10-39-SLR, filed Apr. 15, 2011.

* cited by examiner

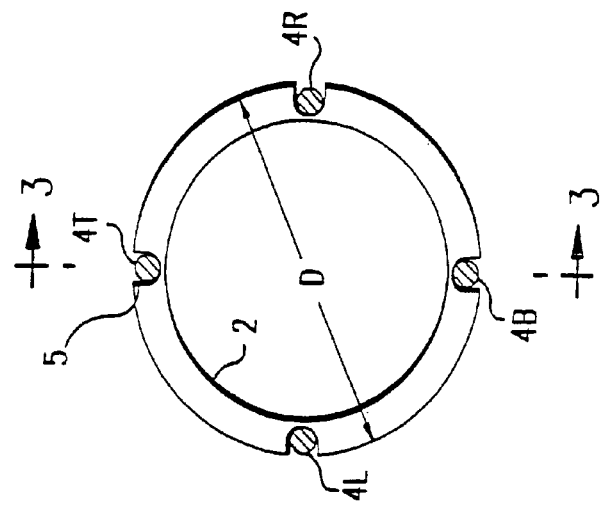
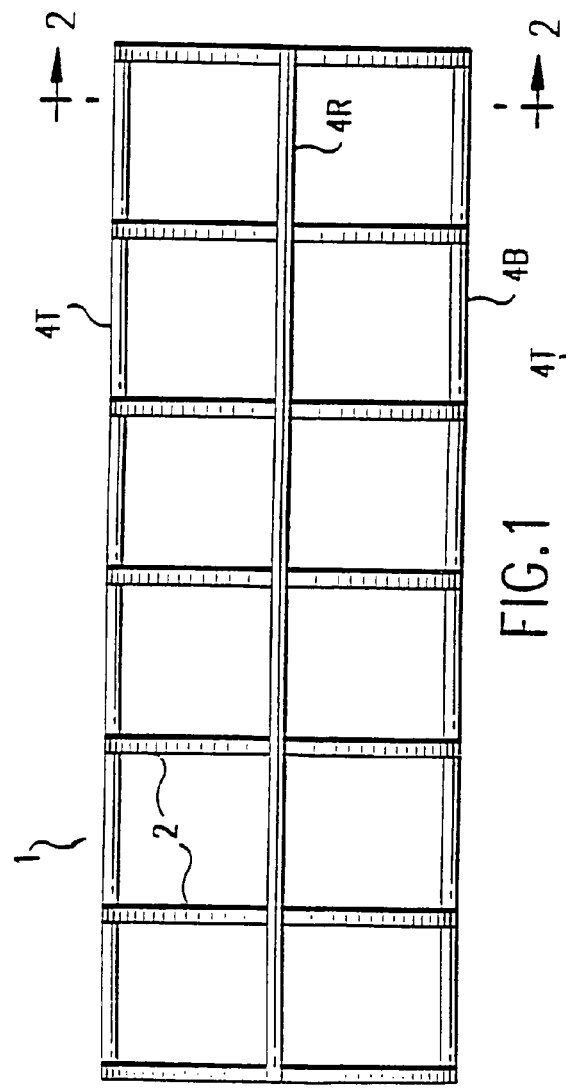
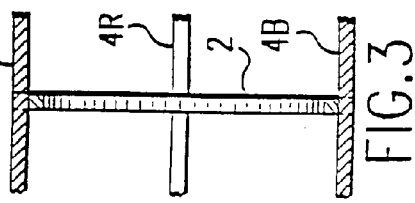
FIG.1
FIG.2
FIG.3

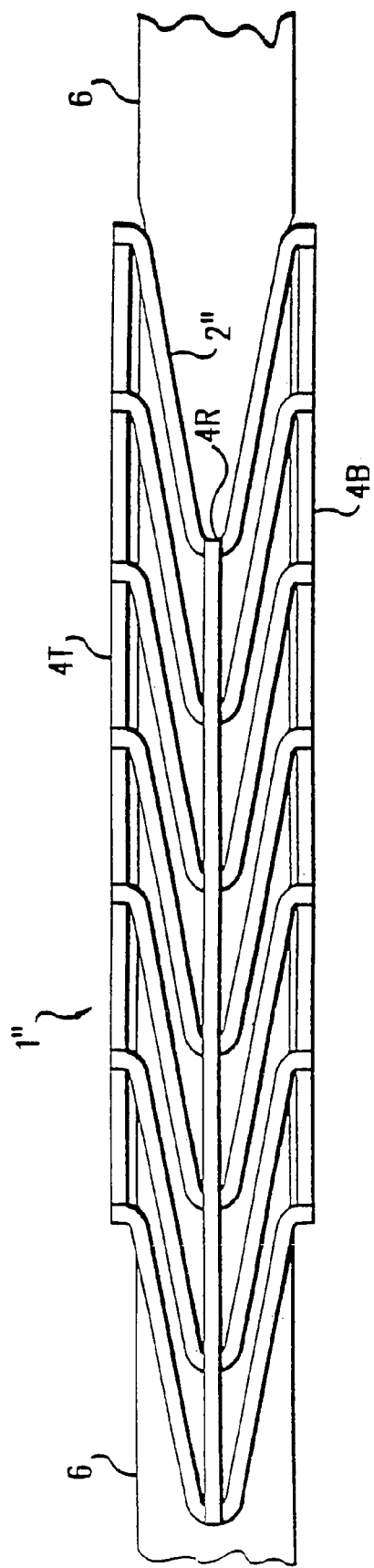
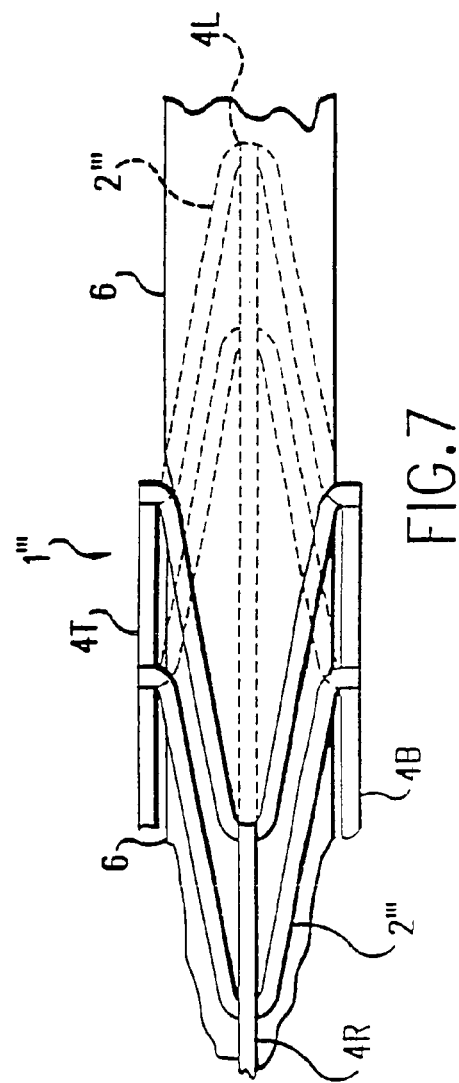
FIG.6
FIG.7

STENT HAVING A MULTIPLICITY OF UNDULATING LONGITUDINALS

CROSS-REFERENCE TO RELATED APPLICATION

This application is a continuation of U.S. application Ser. No. 11/179,424, filed Jul. 12, 2005, which is a continuation of U.S. application Ser. No. 10/662,792 filed Sep. 15, 2003, now abandoned, which is a continuation of U.S. patent application Ser. No. 10/345,531, filed Jan. 16, 2003, now U.S. Pat. No. 6,716,240, which is a continuation of U.S. patent application Ser. No. 09/596,074, filed Jun. 16, 2000, now U.S. Pat. No. 6,547,817, which is a continuation of U.S. patent application Ser. No. 09/263,518, filed Mar. 5, 1999, now U.S. Pat. No. 6,086,604, which is a continuation of U.S. patent application Ser. No. 08/864,221, filed May 28, 1997, now U.S. Pat. No. 5,879,370, which is a continuation of U.S. patent application Ser. No. 08/202,128, filed Feb. 25, 1994, now U.S. Pat. No. 5,643,312.

FIELD OF THE INVENTION

This invention is in the field of stents for maintaining patency of any one of a multiplicity of vessels of the human body.

BACKGROUND OF THE INVENTION

In the last decade, many different designs of stents have been used to maintain patency of arteries and other vessels of the human body. In all such devices, hoop strength is an important characteristic. Specifically, the stent must have enough hoop strength to resist the elastic recoil exerted by the vessel into which the stent is placed. The Mass stent described in the U.S. Pat. No. 4,553,545 and the Dotter stent described in U.S. Pat. No. 4,503,569 are each open helical coils. The Palmaz stent described in the U.S. Pat. No. 4,733,665 is of the "chinese finger" design. The Gianturco-Rubin stent currently sold by Cook, Inc, is another stent design which like the stents of Mass, Dotter and Palmaz does not have any closed circular member to optimize hoop strength.

The ideal arterial stent utilizes a minimum wire size of the stent elements to minimize thrombosis at the stent site after implantation. The ideal arterial stent also possess sufficient hoop strength to resist elastic recoil of the artery. Although the optimum design for maximizing hoop strength is a closed circular structure, no prior art stent has been described which has a small diameter when percutaneously inserted into a vessel and which expands into the form of multiplicity of closed circular structures (i.e. rings) when expanded outward against the vessel wall.

BRIEF SUMMARY OF THE PRESENT INVENTION

The present invention is an expandable stent that can be used in an artery or any other vessel of the human body which, when expanded, forms a multiplicity of generally circular rings whose closed structure optimizes hoop strength so as to minimize elastic recoil of the vessel into which the stent is inserted. Furthermore, the structure of the stent in the present invention is initially in the form of folded ellipses or ovals which can be formed to a small diameter for percutaneous insertion by means of a stent delivery catheter. The ovals are joined to each other by either a straight or undulating shaped wires which are called "longitudinals" which serve to space the deployed rings within the vessel. Straight longitudinals are used in straight vessels and undulating longitudinals can be employed in either straight or highly curved vessels such as some coronary arteries.

Thus, an object of this invention is to provide a stent having a maximum hoop strength by the employment of closed, generally circular structures which are in fact rings.

Another object of this invention is that the rings are initially in the form of ovals that can be folded to fit onto a cylindrical structure at a distal portion of a stent delivery catheter.

Still another object of this invention is that the fully deployed rings are spaced apart by means of longitudinals which are either straight of undulating wires that are placed to be generally parallel to the longitudinal axis of the vessel into which the stent is deployed.

Still another object of this invention is that the pre-deployment stent structure is formed as a single piece out of a metal tube having a smaller inside diameter as compared to the outside diameter of an expandable balloon onto which the pre-deployment stent is mounted.

These and other important objects and advantages of this invention will become apparent from the detailed description of the invention and the associated drawings provided herein.

BRIEF DESCRIPTION OF THE DRAWINGS

FIG. 1 is a side view of the stent after it has been deployed; i.e., in its post-deployment form.

FIG. 2 is a transverse cross section of section 2-2 of FIG. 1 illustrating how the longitudinals are joined to the rings.

FIG. 3 is a cross section at section 3-3 of FIG. 2 showing the joining of a single ring to the longitudinals.

FIG. 6 is a side view of a pre-deployment form of the stent structure in which the ovals have been folded into a small diameter cylinder that is placed around a deflated balloon situated near the distal end of a stent delivery catheter.

FIG. 7 is a partial side-view of a pre-deployment stent structure showing only two of a multiplicity of folded ovals formed around an expandable balloon in which the ovals are folded in an alternative manner as compared with FIG. 6.

DETAILED DESCRIPTION OF THE DRAWINGS

Figure 5:
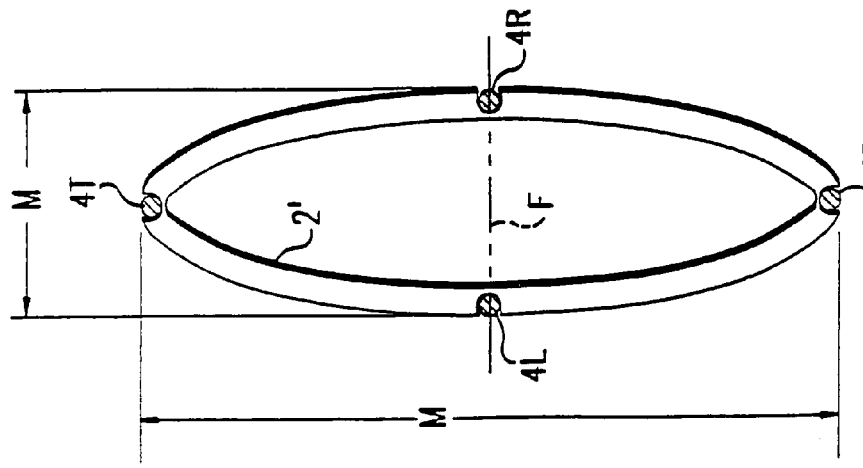
FIG. 5 is a transverse cross section of section 5-5 of FIG. 4 illustrating how the longitudinals are joined to the ovals.

FIG. 1 is a side view of the cylindrical stent 1 of the present invention shown in its post-deployment configuration. The stent 1 has a multiplicity of rings 2 which are spaced apart by four wires called longitudinals. As seen in FIGS. 1 and 2, at the top of the stent is longitudinal 4T, at the bottom is longitudinal 4B, at the left side is longitudinal 4L and at the right side is longitudinal 4R. Although FIGS. 1 and 2 show 7 rings and 4 longitudinals, it is apparent that the stent can be made longer by adding rings or increasing the separation between rings. In a similar manner, the stent can be made shorter by reducing the number of rings or decreasing the spacing between rings. Also variable spacing of the rings is envisioned for accomplishing a variety of purposes including increased hoop strength at a particular section of the stent.

Also, it is envisioned that the two or more longitudinals could be utilized for this stent design with a maximum number being 32.

FIGS. 2 and 3 illustrate the joining of the longitudinals to the rings. Specifically the longitudinals can be placed into cutouts in the form of notches 5 located on the outside perimeter of the ring 2. The longitudinals can then be spot welded, adhesively bonded or joined by any variety of means to the rings 2. It is also envisioned that the longitudinals could be placed on the inside perimeter of the ring 2, or holes could be mechanically or laser drilled through the ring 2 for placement therethrough of the longitudinals.

Figure 4:
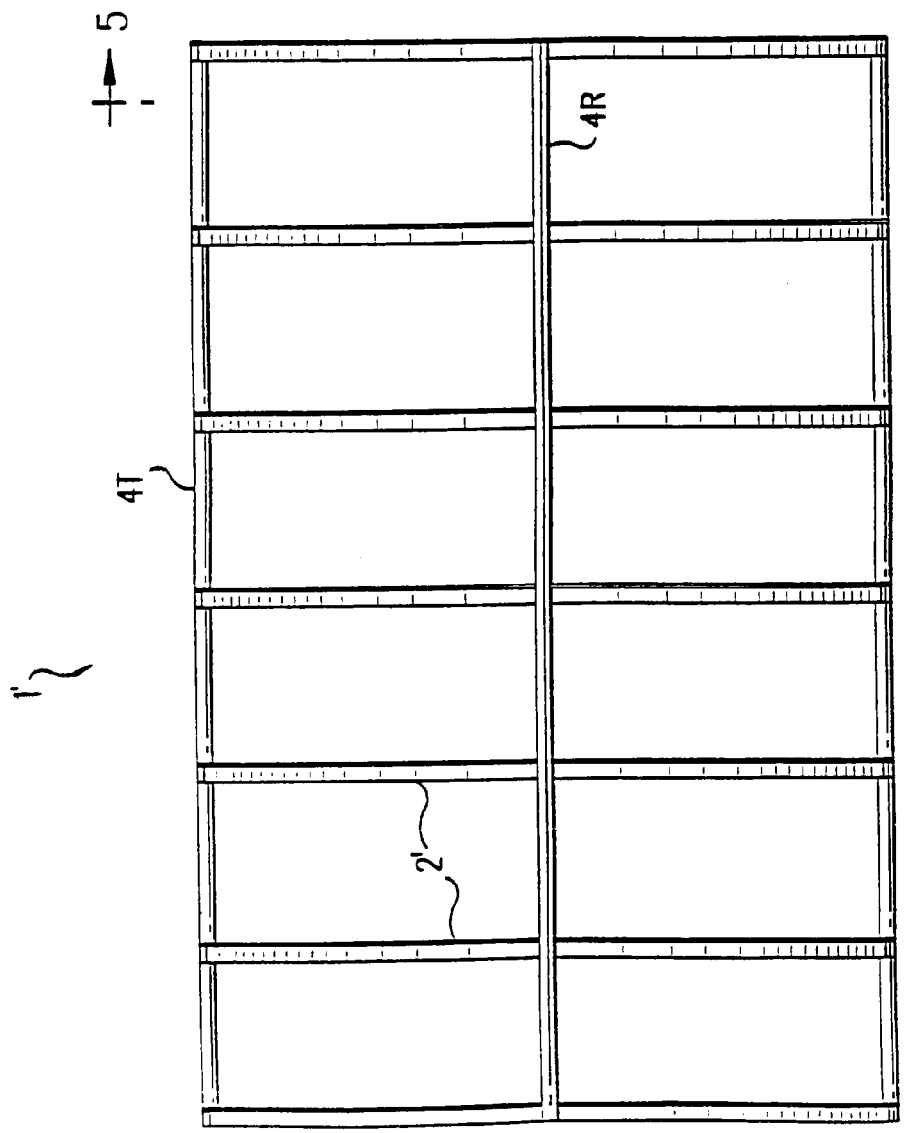
FIG. 4 is a side view of the stent prior to being mounted onto a stent delivery catheter, i.e., in the form of an initial structure.

FIGS. 4 and 5 illustrate a stent 1' shown in one particular form in which it could be fabricated; i.e., in an initial structure form. Specifically, FIGS. 4 and 5 show that this initial form of the stent 1' is a multiplicity of parallel ellipses or ovals 2'' each oval having the same minor axis dimension m and major axis dimension M. The oval's minor axis passes through the center of the longitudinals 4L and 4R. The oval's major axis passes through the center of the longitudinals 4T and 4B. It is important to note that, if it is desired to have a final outside diameter D (as seen in FIG. 2) of the ring 2 after it is fully deployed, then it can be shown that D is given by the equation $D^2 = \frac{1}{2}(m^2 + M^2)$.

To place the stent design of FIGS. 4 and 5 onto a balloon that is mounted near the distal end of a stent delivery catheter, it is necessary to fold the ovals 2' around that balloon. Specifically, the pre-deployment cylindrical stent 1'' can be formed onto an expandable balloon 6 as shown in FIG. 6 by folding the ovals 2' about the dotted line F (which is the minor axis of the oval 2') as shown in FIG. 5 Specifically, as seen in FIG. 4, the top and bottom of the ovals 2' could be held stationery while the side longitudinals 4R and 4L are pushed to the left which results in the pre-deployment structure which is shown as the stent 1'' in FIG. 6. An optimum design has the folded ovals 2'' as shown in FIG. 6 with the stent 1'' being a cylinder whose outside diameter is equal in size to the minor axis dimension m. When the balloon 6 of FIG. 6 is expanded, the pre-deployment stent 1'' structure forms the post-deployment stent 1 structure having circular rings 2 as shown in FIGS. 1 and 2.

The stent 1''' is an alternative embodiment for a pre-deployment structure of the stent of the present invention as it is placed onto a balloon. Specifically, FIG. 7 shows 2 folded rings 2''' of a multiple ring stent 1'''. The stent 1''' being formed by holding the top and bottom of the stent 1' of FIG. 4 stationery while pushing the longitudinal 4R to the left and pushing the longitudinal 4L to the right. Like the stent 1'' of FIG. 6, when mounted onto a balloon, the stent 1''' has cylindrical shape with a diameter equal to the dimension m.

Figure 8:
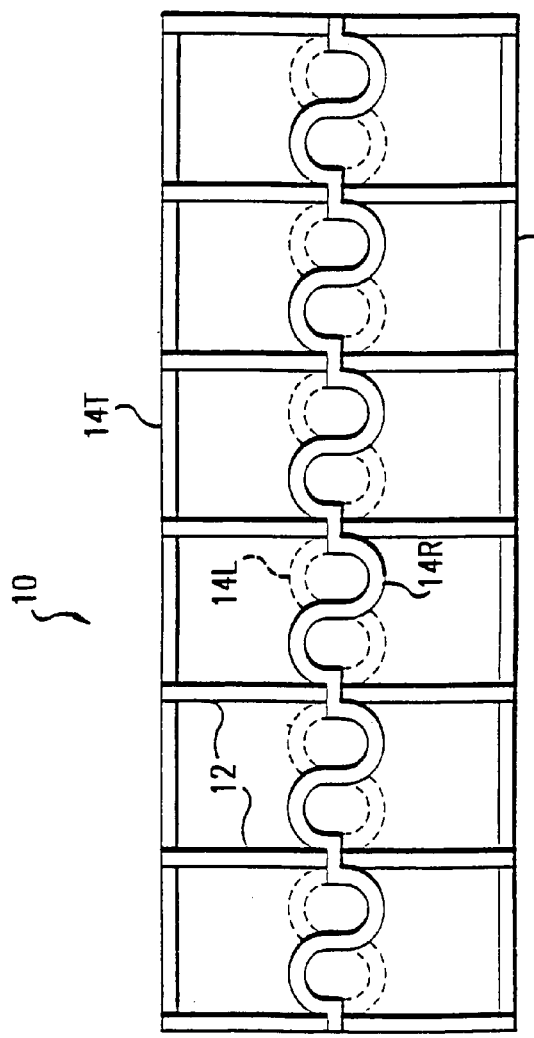
FIG. 8 is a side view of a post-deployment stent structure which utilizes two undulating longitudinals on opposite sides of the stent for improved placement in curved vessels.

FIGS. 1 to 7 inclusive illustrate stents that employ longitudinals that are formed from generally straight wires. FIG. 8 shows an alternative embodiment of a stent 10 that has two undulating longitudinals. Specifically, the left side longitudinal 14L (shown as dotted lines) and the right side longitudinal 14R are each undulating shaped longitudinals. A stent such as stent 10 could have two or more undulating longitudinals. Such a stent would bend more easily during insertion into a vessel and would be more readily adaptable for placement in curved vessels such as some coronary arteries.

Typically, the rings and longitudinals of the stents would be made of the same material. Typical metals used for such a stent would be stainless steel, tantulum, titanium, or a shape memory metal such as Nitinol. If Nitinol is used, the stent would be heat treated into the shape at body temperature having circular rings 2 as shown in FIGS. 1 and 2. The rings could then be distorted into ovals as shown in FIGS. 4 and 5 and then mounted onto a stent delivery catheter which does not employ a balloon but is of the more general shape described in the previously cited U.S. Pat. No. 4,553,545 by C. T. Dotter. Such a design would provide the desired stent structure having a multiplicity of generally circular rings instead of the Dotter design of a helical spring which inherently has a lesser hoop strength as compared to the present invention.

It should be understood that once the ovals are folded onto a stent delivery catheter, when they fully deploy, they do not form perfectly circular rings as shown in FIG. 2, but rather they are of a generally circular shape. Such comparatively small deviations form an exactly circular shape do not appreciably decrease hoop strength because they are in fact closed structures that are almost exactly circular.

It should also be understood that at least part of the end rings of the stent could be fabricated from or coated with a radiopaque metal such as tantalum or gold to provide a fluoroscopic indication of the stent position within a vessel. However, the other rings and the longitudinals could be made from a much less dense metal which would provide less obscuration of the central region within the stent. For example, the stent rings and longitudinals could all be fabricated from titanium or a titanium alloy except the end rings which could be formed from gold which is then plated with titanium. Thus, the entire outside surface of the stent would be titanium, which is known to be a comparatively non-thrombogenic metal while the gold in the end rings provides an improved fluoroscopic image of the stent extremities.

The dimensions of stent rings are typically 0.1 to 0.3 mm thick, with a width of 0.1 to 0.5 mm and an outside diameter D between 2.0 and 30.0; mm depending on the luminal diameter of the vessel into which it is inserted. The length of the stent could be between 1 and 10 cm. The wire diameter for the longitudinals would typically be between 0.05 and 0.5 mm.

Although the designs of FIGS. 1 through 7 inclusive illustrate separate longitudinals attached to a multiplicity of rings, this invention also contemplates an initial stent structure which is chemically etched from thin-walled tubing having an oval transverse cross section. Thus the oval and longitudinals would be formed from a single piece of metal thus precluding the need for attaching the longitudinals to the rings. In a similar manner laser or EDM machining could be used to form the stent from a thin-walled tube.

Figure 9:
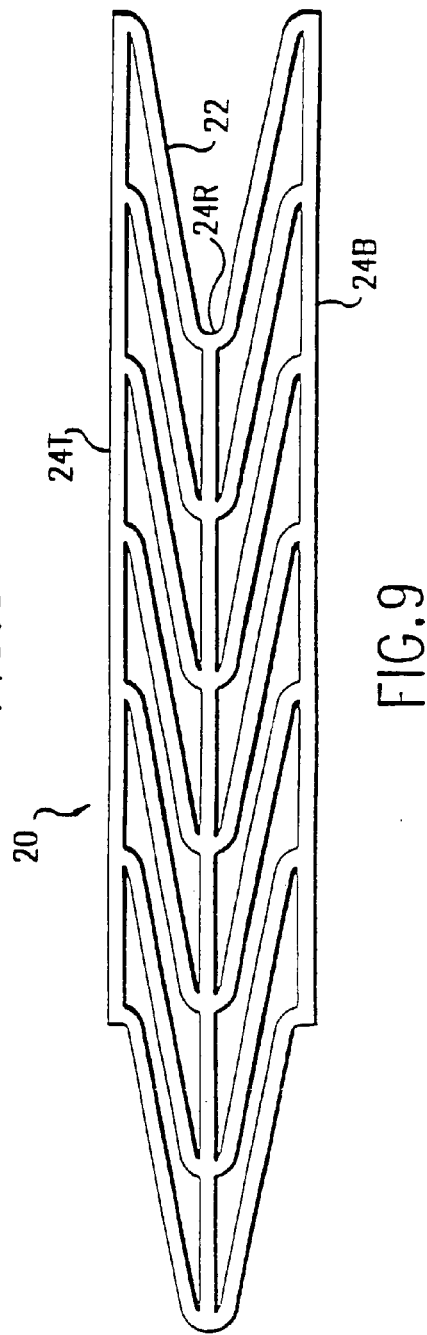
FIG. 9 is a side view of a stent as etched out of a small diameter metal cylinder as a single piece of metal.

It is further anticipated that a pre-deployment stent structure 20 as shown in FIG. 9 could be formed from a thin-walled cylindrical tube whose inside diameter is slightly smaller than the outside diameter of the balloon 6 shown in FIG. 6. A pattern such as that shown in either FIG. 6 or FIG. 7 could be photoetched onto a tin-walled metal cylinder. The one piece structure 20 shown in FIG. 9 has folded ovals 22 and longitudinals 23T, 24B, 24R and (not shown) 24L. This pre-deployment stent structure 20 could then be mounted onto the expandable balloon; the stent having sufficient elastic recoil to firmly grasp down onto the balloon. Another method to form the pre-deployment stent is by etching the correct pattern onto a thin, flat metal plate, then forming a tube from the plate and then making a longitudinal weld to form a cylindrically shaped structure which is, in fact, the pre-deployment stent structure 20 shown in FIG. 9.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A generally cylindrical, balloon-expandable stent for delivery to a desired location in a curved coronary artery on a stent delivery balloon catheter, said stent having a first pre-deployment linear configuration and diameter and a second deployed diameter, wherein the stent is deformed beyond its elastic limit, said stent having a circumference, and a longitudinal axis, said stent having sufficient flexibility to permit intraluminal delivery to the curved coronary artery; said stent in its first diameter comprising: at least two longitudinally spaced apart circumferential rings having closed ends, each of said circumferential rings defining a portion of the circumference of the stent, each of said circumferential rings having at least two peak segments and at least two valley segments; and at least one longitudinally extending connector having a first end portion and a second end portion, said first end portion being fixedly connected to a first of said circumferential rings and said second end portion being fixedly connected to one of said circumferential rings adjacent to said first circumferential ring, said at least one connector having at least one circumferentially and longitudinally arcuate central portion between its first and second end portions so that the at least one connector can expand or contract in length as measured by the straight line distance between its first and second end portions, while being passed through the curved coronary artery.

2. The stent as set forth in claim 1, wherein: a line drawn from said first end portion of said at least on connector to said second end portion of said at least one connector is substantially parallel to the longitudinal axis of the stent.

3. The stent as set forth in claim 1, wherein: there are three of the at least one connectors connecting said first circumferential ring and one of said circumferential rings adjacent to said first circumferential ring.

4. The stent as set forth in claim 1, wherein: said at least one connector has at least two arcuate portions between its first and second end portions.

5. The stent as set forth in claim 1, wherein: the first end portion of said at least one connector is connected to one of the at least two peak segments of said first circumferential ring and the second end portion of said at least one connector is connected to one of the at least two valley portions of one of said circumferential rings adjacent said first circumferential ring.

6. The stent as set forth in claim 5, wherein: the arcuate portion of said at least one connector is located entirely within one of the at least two valley portions of one of said circumferential rings adjacent said first circumferential ring.

7. The stent as set forth in claim 1, wherein: said arcuate portion of said at least one connector includes at least one generally U-shaped segment.

8. The stent as set forth in claim 7, wherein: said arcuate portion of said at least one connector includes at least two generally U-shaped segments that open in opposite directions.

9. The stent as set forth in claim 8, wherein: at least two of said generally U-shaped segments are positioned adjacent to one another, each of said generally U-shaped segments include a pair of spaced apart legs joined by an arcuate section, and one of the legs of one of the U-shaped segments is coextensive with one of the legs of one of the other U-shaped segments.

* * * * *